(12) United States Patent
Zahalsky (10) Patent No.: US 11,324,780 B2
(45) Date of Patent: May 10, 2022

(54) AMNIOTIC FLUID COMPOSITION AND METHOD OF USING

(71) Applicant: Michael P. Zahalsky, Parkland, FL (US)

(72) Inventor: Michael P. Zahalsky, Parkland, FL (US)

( * ) Notice: Subject to any disclaimer, the term of this patent is extended or adjusted under 35 U.S.C. 154(b) by 414 days.

(21) Appl. No.: 16/175,042

(22) Filed: Oct. 30, 2018

(65) Prior Publication Data

US 2019/0060372 A1 Feb. 28, 2019

Related U.S. Application Data

(60) Continuation-in-part of application No. 15/158,101, filed on May 18, 2016, now Pat. No. 10,548,925, which is a division of application No. 14/363,142, filed as application No. PCT/US2013/023830 on Jan. 30, 2013, now Pat. No. 10,751,374, which is a continuation-in-part of application No. 15/541,988, filed as application No. PCT/US2016/016934 on Feb. 8, 2016, now abandoned.

(60) Provisional application No. 61/592,108, filed on Jan. 30, 2012, provisional application No. 62/112,709, filed on Feb. 6, 2015.

(51) Int. Cl.
| | |
|---|---|
| *A61K 38/18* | (2006.01) |
| *A61K 35/48* | (2015.01) |
| *A61L 27/38* | (2006.01) |
| *A61L 27/54* | (2006.01) |
| *A61K 9/00* | (2006.01) |
| *A61K 38/24* | (2006.01) |
| *A61K 38/27* | (2006.01) |
| *A61K 35/50* | (2015.01) |
| *A61K 45/06* | (2006.01) |
| *C12N 5/00* | (2006.01) |
| *A61K 38/09* | (2006.01) |
| *A61K 35/16* | (2015.01) |
| *A61K 35/545* | (2015.01) |
| *A61K 31/568* | (2006.01) |
| *A61K 47/42* | (2017.01) |
| *A61L 27/58* | (2006.01) |
| *C12N 5/071* | (2010.01) |
| *A61L 27/36* | (2006.01) |
| *A61K 35/28* | (2015.01) |
| *A61K 35/35* | (2015.01) |
| *A61L 27/22* | (2006.01) |
| *A61L 27/24* | (2006.01) |
| *C12N 5/0775* | (2010.01) |

(52) U.S. Cl.
CPC ............ *A61K 35/48* (2013.01); *A61K 9/0019* (2013.01); *A61K 9/0024* (2013.01); *A61K 9/0034* (2013.01); *A61K 31/568* (2013.01); *A61K 35/16* (2013.01); *A61K 35/28* (2013.01); *A61K 35/35* (2013.01); *A61K 35/50* (2013.01); *A61K 35/545* (2013.01); *A61K 38/09* (2013.01); *A61K 38/18* (2013.01); *A61K 38/24* (2013.01); *A61K 38/27* (2013.01); *A61K 45/06* (2013.01); *A61K 47/42* (2013.01); *A61L 27/225* (2013.01); *A61L 27/24* (2013.01); *A61L 27/3633* (2013.01); *A61L 27/3834* (2013.01); *A61L 27/54* (2013.01); *A61L 27/58* (2013.01); *C12N 5/00* (2013.01); *C12N 5/0667* (2013.01); *C12N 5/0683* (2013.01); *A61L 2300/41* (2013.01); *A61L 2300/414* (2013.01); *A61L 2400/06* (2013.01)

(58) Field of Classification Search
CPC .... A61K 38/18; A61K 9/0019; A61K 9/0034; A61K 35/50; A61K 35/545; A61K 35/28; A61K 35/48; A61L 27/3633; A61L 27/3834; A61L 27/54; A61L 2300/414
See application file for complete search history.

(56) References Cited

U.S. PATENT DOCUMENTS

| | | |
|---|---|---|
| 6,022,539 A | 2/2000 | Wegman |
| 7,501,115 B2 | 3/2009 | Fraser et al. |
| 7,687,059 B2 | 3/2010 | Fraser et al. |
| 2009/0311223 A1 | 12/2009 | Ichim |

(Continued)

FOREIGN PATENT DOCUMENTS

| | | |
|---|---|---|
| WO | 2009120879 | 10/2009 |
| WO | 2011109026 | 9/2011 |
| WO | 2013116327 | 8/2013 |

OTHER PUBLICATIONS

Zahalsky et al. Amniotic Fluid for the Treatment of Erectile Dysfunction. The Journal of Urology. 2017;197(4S): e540-e541.*

(Continued)

*Primary Examiner* — Lynn Y Fan
(74) *Attorney, Agent, or Firm* — David L. King (57) ABSTRACT

A composition for treating a patient with a tissue disease or malformity has a composition containing amniotic fluid. The amniotic fluid has a quantity of gender specific amniotic fluid based on a gender of a fetal source. A method of treating a patient with a tissue disease or malformity comprises the steps of: identifying the tissue region to be treated and selecting a location to apply either topically or by injection or inhalation a composition containing amniotic fluid; selecting the composition containing amniotic fluid wherein the amniotic fluid has a quantity of gender specific amniotic fluid based on a gender of a fetal source allowing more specific targeted growth factors to be used for specific disease processes; and applying or injecting the composition at or into the selected location.

6 Claims, 8 Drawing Sheets

(56) References Cited

U.S. PATENT DOCUMENTS

2011/0218396 A1     9/2011    Williams
2012/0183519 A1     7/2012    Swift

OTHER PUBLICATIONS

Desai et al. Penile Injection Instructions. Potomac Urology. 2016;1-3.*

Injection. Peyronie's disease: diagnostic work-up and treatment. Urology—textbook. 2010; 1-8.

Tunica. Peyronie's disease: causes and symptoms. Urology—textbook. 2010; 1-4.

Zhang, et al; "Stem Cells; novel players in the treatment of erectile dysfunction". Asian Journal of Andrology (Jan. 2012) vol. 14, No. 1, pp. 145-155, p. 148 col 2 para2.

Alexander et al., Separating Stem Cells by Flow Cytometry: Reducing Variability for Solid Tissues, Cell Stem Cell, (2009), pp. 579-583 and suppl. mater, vol. 5.

Cytori Therapeutics, Study of Autologous Fat Enhanced with Regenerative Cells Transplanted to Reconstruct Breast Deformities after Lumpectomy (RESTORE-2), Clinical Trial, (2011).

Frantz et al., The Extracellular Matrix at a Glance, J Cell Sci, (2010), pp. 4195-4200, vol. 123, No. 24.

Gimble et al., Adipose-Derived Stem Cells for Regenerative Medicine, Gire. Res., (2007), pp. 1249-1260, vol. 100.

Hauck et al., A Critical Analysis of Nonsurgical Treatment of Peyronie's Disease, Eur. Urol., (2006), pp. 987-997, vol. 49.

Kendirci et al., Transplantation of Non-Hematopoietic Adult Bone Marrow Stem/Progenitor Cells Isolated by the p75 Nerve Growth Factor Receptor into the Penis Rescues Erectile Function in a Rat Model of Cavernous Nerve Injury, J_Urol., (2010), pp. 1560-1566, vol. 184, No. 4.

Kondo et al., Implantation of Adipose-Derived Regenerative Cells Enhances Ischemia-Induced Angiogenesis, Arteriosclerosis, Thrombosis, and Vase. Biol., (2009), pp. 61-66, vol. 29.

Ma et al., Adipose Tissue-Derived Stem Cell-Seeded Small Intestinal Submucosa for Tunica Albuginea Grafting and Reconstruction, PNAS, (2012), pp. 2090-2095, vol. 109, No. 6.

Meyerrose et al., In Vivo Distribution of Human Adipose-Derived Mesenchymal Stem Cells in Novel Xenotransplantation Models, Stem Cells, (2007), pp. 220-227, vol. 25.

Thomas. Stem Cells Repair Damaged Corneas in Mice. HealingWell.com (http://news.healingwell.com/index.php?p=news1&id=625948) (2009).

Turksen Ed.. Embryonic Stem Cells: Methods and Protocols. (2002). vol. 185, Humana Press.

Weiler-Mithoff et al., Single Treatment Cell-Enhanced Reconstruction After BCT: a Proven Technique (Early outcomes of RESTORE-2), Thirty-Second Annual CTRC-AACR San Antonio Breast Cancer Symposium, (2009).

Woo et al., Transplantation of Muscle-Derived Stem Cells into the Corpus Cavemosum Restores Erectile Function in a Rat Model of Cavernous Nerve Injury, Korean J Ural, (2011), pp. 359-363, vol. 52.

Hellstrom WG. Medical management of Peyronie's disease; J Androl; 2009;30:397-405.

Zhang et al; "Preservation of the cardiac function in infarcted rat hearts by the transplantation of adipose-derived stem cells with injectable fibrin scaffolds"; Experimental Biology and Medicine 2010; 235: 1505-1515. DOI: 10.1258/ebm.20103010175.

Del Carlo M, et al; "Differential Calcium Independent Regulation of Matrix Metalloproteinases and Tissue Inhibitors of Matrix Metalloproteinases by Interleukin-1β and Transforming Growth Factor-β in Peyronie's Plaque Fibroblasts"; Journal of Urology 2008; vol. 179, issue 6, pp. 2447-2455.

* cited by examiner

|    |      |      | Change |
|----|------|------|--------|
| RH | 32.1 | 38.8 | 6.7    |
| EB | 0    | 16.8 | 16.8   |
| MN | 12.9 | 15.5 | 2.6    |
| CM | 38.2 | 42.1 | 3.9    |
| AK | 46.5 | 54.6 | 8.1    |

AMNIOTIC FLUID COMPOSITION AND METHOD OF USING

RELATED APPLICATIONS

The present invention is a continuation in part of U.S. Ser. No. 15/158,101 entitled "Methods And Composition For Treatment Of Penile Defects" filed on May 18, 2016 which is a division of U.S. Ser. No. 14/363,142 filed on Jun. 5, 2014 which is a national stage entry of PCT/US2013/023830 filed on Jan. 30, 2013 which claims priority to 61/592,108 filed on Jan. 30, 2012 and a continuation in part of U.S. Ser. No. 15/541,988 entitled, "Methods And Compositions For Treatment Of Penile Defects" filed on Jul. 6, 2017 which is a national stage entry of PCT/US2016/016934 filed on Feb. 8, 2016 which claims priority to 62/112,709 filed on Feb. 6, 2015.

TECHNICAL FIELD

The present invention relates to a composition and method of treating tissue disease or malformities in the tissue or treating disease processes by having the composition include growth factors found in amniotic fluid, more particularly a gender differentiated amniotic fluid. The Invention relates to being able to treat different specific diseases by different types of Amniotic Fluid that is rich in different specific growth factors. The invention relates to the selectivity process that allows us to harness more specific growth factors for specific diseases and is unique and never done before.

BACKGROUND OF THE INVENTION

The use of amniotic fluid to treat a variety of tissue disorders is well known and commonly practiced. There are however, a number of indications and treatments where the use of amniotic fluid has not been attempted for a variety of reasons. There are a number of areas where the results of treatments have been at best unpredictable for a variety of reasons based mostly on speculation and conjecture. As a result, the use of amniotic fluid has had mixed reviews.

Within the uterus of a pregnant woman, a growing fetus is surrounded and cushioned by amniotic fluid, a watery liquid within the amnion Amniotic fluid is one of the main samples used for the medical examination of the pregnant woman and her fetus.

Traditionally, during a Caesarean section, after cutting through the uterus, the amniotic fluid will be suctioned away and discarded to make more room Amniotic fluid contains cells, electrolytes, growth factors, carbohydrates, lipids, proteins, amino acids, lactate, pyruvate, enzymes and hormones Amniotic fluid is also a source of stem cells which ideally should be isolated and separately cultivated for cell therapy purposes. While amniotic fluid cells can be obtained from a small amount of fluid during amniocentesis, these amounts are insufficient for a larger scale harvesting of biomolecules or culturing of the stem cells comprising amniotic fluid.

In US 2015/0025366 entitled "Method for Obtaining Sterile Human Amniotic Fluid and Uses Thereof" published Jan. 22, 2015 stated, there is a recognized need in the art for an improved means for obtaining sterile amniotic fluid for use in research and the development of therapeutic products. Particularly, the prior art is deficient in methods for obtaining sterile human amniotic fluid with minimal or no risk to a pregnant woman or fetus by collecting the amniotic fluid prior to an elective Caesarean section. Also, the prior art is deficient in methods for obtaining sterile human amniotic fluid devoid of cells which may create unwanted reactions due to their allogenic characters on the patients to be treated. The inventor, Harrell, claimed to fulfill this longstanding need and desire in the art to improve the safety of amniotic fluid in its medical uses and taught how to sterile filter the fluid.

This prior art method of obtaining sterile filtered human amniotic fluid from an individual comprises the steps of obtaining sterile human amniotic fluid from an individual, removing cells, large particles and other undissolvables from said human amniotic fluid by high speed centrifugation, followed by membrane filtration. The first step is to centrifuge the amniotic fluid in swing out buckets adapted to swing out rotors or other centrifugation bottles in angle rotors at about 5,000 rpm to about 10,000 rpm for about 30 minutes to about 60 minutes. The supernatant is then filtered using filters with a pore size of about 5 µm to about 10 µm to obtain the first filtrate, then filtering said first filtrate through filters with a pore size of about 1.0 µm to obtain a second filtrate, filtering the second filtrate through filters with the pore size of 0.45 µm or/and 0.2 µm to obtain a sterilely filtered amniotic fluid. In case of a final membrane filtration limited to 0.45 µm, it is preferable to repeat a second filtration on a second 0.45 µm membrane, to increase the sterility assurance level. The sterile amniotic fluid retains the growth factors from the raw amniotic fluid. In this method, the first centrifugation step may be replaced by depth filtration through available filtration systems, however this option is not preferred because it leads to important volume losses and undesirable adsorption of growth factors by the filtration media.

This technique disclosed by Harrell achieved a sterile fluid that removed all particles down to 0.2 micron. All cells and particulate greater than the 0.2 micron are removed, leaving a fluid devoid of much of the beneficial biochemical particles needed to be useful in medical treatments.

An improved method of recovering amniotic fluid is described in US 2017/0042943 A1 entitled "Liquid Amnion Transplant Product", that invention discloses a method to recover amniotic fluid and maintain particles in sizes up to 170 microns to 260 microns, over 100 times greater, but maintaining a non-immunogenic product having superior biochemical properties suitable for direct injection into patients.

The present invention is believed to have established, at least in some treatment protocols, a novel and heretofore unexpected way to maximize the use of recovered amniotic fluids suitable for direct injection or as a topical ointment that will be more reliable and have better positive outcomes.

One area of interest is that of penile defects, such as erectile dysfunction (ED) and Peyronie's disease. At least some forms of ED trace their etiology to vascular deficits in the penile tissue. Pharmaceutical compositions for treating ED do exist; however, a need exists for more advanced treatments that may require use of medicaments. At least one group has reported success in the use of stem cells derived from bone marrow to reverse ED in an animal model. Kendirci M et al. Transplantation of non-hematopoietic adult bone marrow stem/progenitor cells isolated by the p75 nerve growth factor receptor into the penis rescues ED in a rat model of cavernous nerve injury. J. Urol. 2010; 184(4): 1560-1566. Another group has seen success in using muscle-derived stem cells in a rat model of ED. Woo J C et al. Transplantation of muscle-derived stem cells into the corpus cavernosum restores erectile function in a rat model of cavernous nerve injury. Korean J. Urol. 2011; 52: 359-363.

Peyronie's disease is an ailment involving the growth of fibrous plaques in the soft tissue of the penis. These plaques grow in the tunica albuginea, a region of connective tissue that is part of the more general connective tissue of Buck's fascia. The tunica albuginea is an area surrounding the corpora cavernosa. The disease results in pain, ED, and alteration of penis shape, and may be caused by disorganized collagen fibers. Treatments for the disease currently include administration of corticosteroids to the plaques, radiation therapy, and vitamin E Pharmaceuticals for treatment exist; however, the use of medicaments is considered controversial in the art, and these compounds have not met with sustained success. Hauck E W et al. A critical analysis of nonsurgical treatment of Peyronie's disease. European Urology 2006; 49(6): 987-97.

To take full advantage of these opportunities, improved capabilities are needed.

In order to correct penile defects such as Peyronie's disease or erectile dysfunction, it is known to inject medications into the tissue of the patient's penis. This procedure can typically be done in a doctor's office under supervision of a trained professional. It is important when injecting the penis that the medications be delivered to the locations in need of treatment while avoiding areas that could cause damage.

Many of the new medications used during these procedures can include biological products such as stem cells or other organic material that needs to be strategically placed along the shaft of the penis.

In some cases, it may be possible for the patient to self-inject himself with medications to assist in the repair and recovery process. The self-injections will most likely occur at the patient's home without supervision of a trained professional. This is very similar to diabetic patients who routinely inject themselves with insulin. In such cases, it is important that the medications be delivered in the proper dosage at the proper location. In some cases, the medication can be topically applied generally, however, implantation or injections seem to be most effective.

The present invention provides a unique method and composition that utilizes amniotic fluid as a critical source to deliver tissue regenerative proteins and growth factors to the tissue in need of repair. The present invention defines a unique selection process to maximize the certain growth factors for certain disease processes. The present invention summarized and described hereinafter provides a unique selection process and use and refinement in treatments employing amniotic fluid.

SUMMARY OF THE INVENTION

A composition for treating a patient with a tissue disease or malformity has a composition containing amniotic fluid. The amniotic fluid has a quantity of gender specific amniotic fluid based on a gender of a fetal source. From this gender source we are now able to get specific growth factors in higher concentrations.

The gender specific amniotic fluid of female fetal source and the male fetal source exhibit about 1451 growth factors and cytokines when tested under mass spectrometry. The female fetal source amniotic fluid exhibits 49 growth factors in a statistically significant higher concentration than the male fetal source amniotic fluid. The male fetal source amniotic fluid exhibits 45 growth factors in a higher concentration than the female fetal source amniotic fluid. Each of the number of growth factors concentration higher in each gender specific amniotic fluid is greater than 25 and less than 50 of the total of about 1500. The female fetal source amniotic fluid has 49 growth factors statistically significantly greater than the male fetal source amniotic fluid. The male fetal source amniotic fluid has 45 growth factors statistically significant greater than the female fetal source amniotic fluid. The selection of the composition with amniotic fluid is guided by differences in growth factors and cytokines between the gender specific amniotic fluids. The gender specific amniotic fluid has a selected proportion of male fetal source amniotic fluid or female fetal source amniotic fluid relative to the total amniotic fluid. The selected proportion of male fetal source or female fetal source amniotic fluid is between 75 percent and up to 100 percent and at 100 percent the amniotic fluid is either all female fetal source or all male fetal source amniotic fluid. The amniotic fluid is further selected based on disease process based upon age of term pre planned C Sections in addition to gender of fetus. The composition wherein 5 or more of the following growth factors or proteins are present in the female fetal source amniotic fluid: NP_001306130.1, NP_002956.1, NP_065723.1, NP_005611.1, NP_005538.2, XP 016870146.1, NP_001531.1, NP_001303936.1, NP_000415.2, NP_775109.2, NP_057274.1, NP_002263.3, NP_705694.2, NP_002267.2, NP_005545.1, NP_001435.1, NP_000587.1, NP_001276737.1, NP_001313.1, NP_444513.1, NP_001186757.1, XP 016880078.1, NP_002696.3, NP_001186652.1, NP_004406.2, XP 016873759.1, NP_002266.2, NP_001005337.1, XP 016881722.1, NP_056932.2, NP_002855.2, NP_005969.1, NP_000688.2, NP_443112.2, NP_001979.2, NP_001116437.1, NP_057215.3, NP_001171712.1, XP 005259194.1, NP_001142.2, NP_009140.1, NP_057671.2, NP_071404.2, NP_001001973.1, NP_114409.2, NP_001132929.1, NP_001135757.1, NP_002943.2, NP_005637.3. Of these, the 5 important growth factors in the treatment of disease or malformities in the penis are XP 016881722.1 (choriogonadotropin subunit beta variant 1 isoform X1), NP_000587.1 (Insulin-like growth factor-binding protein 1; prolongs the half-life of the IGFs and alters their interaction with cell surface receptors), NP_001531.1 (Heat shock protein 27; provide thermotolerance in vivo, cyto-protection, and support of cell survival under stress conditions, stabilizing partially denatured proteins, protects actin filaments from fragmentation), XP_016870146.1 (Annexin Al; inhibits various leukocyte inflammatory events, inhibit the two main products of inflammation, effect being much like that of NSAIDs, potentiating the anti-inflammatory effect), NP_000415.2 (Keratin 5; in the stratified epithelium lining the skin and digestive tract forms the intermediate filaments (IF) that make up the cytoskeleton of basal epithelial cells, increases the elasticity). In addition, these other growth factors are important: NP_005545.1 (Keratin 6A; shown to have antimicrobial properties, and is the main antimicrobial factor in the eye), NP_001276737 (Alpha-crystallin B chain; bind improperly folded proteins to prevent protein aggregation, confer stress resistance to cells by inhibiting the processing of the pro-apoptotic protein caspase-3, increased during various stresses, which then may lead to prolonged survival of cells under these conditions), NP_001313.1 (Cystatin-SA; found in a variety of human fluids and secretions, where they appear to provide protective functions), NP_444513.1 (Dermcidin, anti-microbial peptides, secreted by human eccrine sweat glands onto the skin as a part of the innate host defense of the immune system), XP 016873759.1 (Neuroblast differentiation-associated protein, neuronal differentiation, elasticity, structural scaffolding), NP_002855.2 (Pregnancy zone protein; role in immune-regulation during pregnancy).

A method of treating a patient with a tissue disease or malformity comprises the steps of: identifying the tissue region to be treated and selecting a location to apply either topically or by injection a composition containing amniotic fluid; selecting the composition containing amniotic fluid wherein the amniotic fluid has a quantity of gender specific amniotic fluid based on a gender of a fetal source; and applying or injecting the composition at or into the selected location.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines or type of stem cell, constructs, additives, and reagents described herein. It is also to be understood that the terminology used herein is for the purpose of describing particular embodiments only, and is not intended to limit the scope of the present invention which will be limited only by the appended claims.

The term "amniotic fluid" refers to the protective liquid contained by the amniotic sac of a gravid Amniote. This fluid serves as a cushion for the growing fetus, but also serves to facilitate the exchange of nutrients, water, and biochemical products between mother and fetus. Recent studies show that amniotic fluid contains a considerable quantity of stem cells. These amniotic stem cells are pluripotent and able to differentiate into various tissues, which may be useful for future human application. Some researchers have found that amniotic fluid is also a plentiful source of non-embryonic stem cells. These cells have demonstrated the ability to differentiate into a number of different cell-types, including brain, liver and bone.

The term "growth factor" refers to a naturally occurring substance capable of stimulating cellular growth, proliferation, healing, and cellular differentiation. Usually it is a protein or a steroid hormone. Growth factors are important for regulating a variety of cellular processes.

The term "protein" refers to large biomolecules, or macromolecules, consisting of one or more long chains of amino acid residues. Proteins perform a vast array of functions within organisms, including catalysing metabolic reactions, DNA replication, responding to stimuli, and transporting molecules from one location to another. Proteins differ from one another primarily in their sequence of amino acids, which is dictated by the nucleotide sequence of their genes, and which usually results in protein folding into a specific three-dimensional structure that determines its activity.

Growth factors typically act as signalling molecules between cells. Examples are cytokines and hormones that bind to specific receptors on the surface of their target cells.

The term "stem cell" refers to any multipotent or pluripotent cell, traditional stem cells, progenitor cells, preprogenitor cells, and reserve cells. The term is used interchangeably with and may mean progenitor cell. The stem cell may be derived from an adult organism or from a cell line, or from an embryonic organism. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including method for isolating and culturing them, may be found in, among other places, Embryonic Stem Cells, Methods and Protocols, Turksen ed., Humana Press, 2002.

The term "adult" as used herein refers to any non-embryonic organism. For example the term "adult adipose-derived regenerative cell," refers to an adipose-derived regenerative cell, other than that obtained from an embryo.

The term "embryo" as used herein refers to any multi-cellular diploid eukaryote during development, until birth or hatching. The term "embryonic stem cell" refers to a pluripotent cell derived from the inner cell mass of a blastocyst.

The term "mesenchymal stem cell" refers to any multi-potent stromal cell derived from, for example and without limitation, umbilical cord blood, adipose tissue, muscle, corneal stroma, and dental pulp that can differentiate into cells such as, including but not limited to, osteoblasts, chondrocytes, and adipocytes.

The term "adipose-derived regenerative cell" (ADRC) is used interchangeably with adipose stem cells (ASC) herein and refers to adult cells that originate from adipose tissue. ADRC are a heterologous population of cells comprising at least one of the following population of cells; adult stem cells, vascular endothelial cells, vascular smooth muscle cells, endothelial cells, mesenchymal stem cells, fibroblasts, pericytes and additional other cell types.

In some embodiments, ADRC refers to a substantially pure population of adipose-derived stem cells. ADRC can be easily harvested from adipose tissue and are substantially free of adipocytes and red blood cells and clonal populations of connective tissue stem cells. The stromal vascular fraction cells are substantially devoid of extracellular matrix material from adipose tissue. ADRC may also be referred to as adipose-derived stem/stromal cells (ASCs), adipose-derived adult stem (ADAS) cells, adipose-derived adult stromal cells, adipose-derived stromal cells, adipose stromal cells, adipose mesenchymal cells, adipose-derived mesenchymal stem cells, lipoblasts, pericytes, preadipocytes, and processed lipoaspirate cells.

The term "adipose" as used herein refers to any fat tissue from a subject. The terms "adipose" and "adipose tissue" are used interchangeably herein. The adipose tissue may be brown fat, white fat or yellow fat or white adipose tissue, derived from subcutaneous, omental/visceral, mammary, gonadal, or other adipose tissue site. The adipose tissue has adipocytes and stroma. Adipose tissue is found throughout the body of an animal. For example, in mammals, adipose tissue is present in the omentum, bone marrow, subcutaneous space, and surrounding most organs. Such cells may comprise a primary cell culture or an immortalized cell line. The adipose tissue may be from any organism having fat tissue.

Preferably, the adipose tissue is human; most preferably, the adipose tissue is derived from the individual in need of treatment for a penile defect. A convenient source of adipose tissue is from liposuction surgery, however, the source of adipose tissue or the method of isolation of adipose tissue is not critical to the invention, and acquisition of adipose tissue by any means may adequately provide tissue and stem cells for the present invention.

The term "tissue" as used herein is a broad term that is applied to any group of cells that perform specific functions, and includes in some instances whole organs and/or part of organs. A tissue need not form a layer, and thus encompasses a wide range of tissue, including adipose tissue derived from any source in an organism. Preferably, the tissue is derived from a mammal. Most preferably, the tissue is derived from the individual in need of treatment for a penile defect.

The term "implant" as used herein refers to any method for transferring a population of cells or cell mass into a subject, including by surgical implantation (incision into the tissue of interest and deposition therein) and injection by a syringe, needle, cannula, or the like of any suitable gauge. An implant as used herein can comprise genetically modified cells, as well as cells differentiated from other cells, such as stem cells, progenitors, and the like, as well as adipose cells or tissue.

The term "corpus cavernosum" of the penis refers to one of a pair of sponge-like regions of erectile tissue which contain most of the blood in the penis during penile erection. Generally, the two corpus cavernosum and a corpus spongiosum are three expandable erectile tissues along the length of the penis which fill with blood during erection. The term "corpus" is used interchangeably herein with corporal, corporeal and corporic, which are terms used to describe tissues which are derived from the corpora cavernosum or which can be developed, differentiated, or altered by natural or artificial means into corpora cavernosum tissue. The term "cavernosum" is used interchangeably herein as cavernae, corporum, cavernosum, or cavernosorum penis, and refers to the caverns of corpora cavernosa (or one of the two corpus cavernosum) of the penis or the dilatable spaces within the corpus cavernosum of the penis, which fill with blood and become distended with erection.

The term "tunica albuginea" refers to the fibrous tissue covering, or enveloping, the corpora cavernosa of the penis. This tissue consists of elastin and collagen. The term "Bucks fascia" refers to the layer of fascia covering the penis, including the tunica albuginea.

The terms "subject", "individual" and "patient" are used interchangeably herein, and refer to an animal, for example a human, from whom a adipose tissue and stem cells, for example ADRC can be harvested, or a subject into whom tissue can be transplanted for treatment, for example treatment for penile defects, using the compositions and methods described herein. For treatment of conditions or disease states which are specific for a specific animal such as a human subject, the term "subject" refers to that specific animal. In some embodiments, the subject is a human subject. It is possible in embodiments of this invention that recipient subjects are of a different mammalian subject than the donor subject.

The term "exosomes" refers to cell-derived vesicles that are present in many and perhaps all eukaryotic fluids, including blood, urine, and cultured medium of cell cultures. Evidence is accumulating that exosomes have specialized functions and play a key role in processes such as coagulation, intercellular signaling, and waste management. Consequently, there is a growing interest in the clinical applications of exosomes. Exosomes can potentially be used for prognosis, for therapy, and as biomarkers for health and disease.

The term "M RNA" refers to a large family of RNA molecules that convey genetic information from DNA to the ribosome, where they specify the amino acid sequence of the protein products of gene expression.

BRIEF DESCRIPTION OF THE DRAWINGS

The invention will be described by way of example and with reference to the accompanying drawings in which.

DETAILED DESCRIPTION OF THE INVENTION

The present invention is directed to a unique use of recovered amniotic fluid for treatment of various tissue conditions. The current use of amniotic fluid for soft tissue is known in the art as disclosed in the publication US 2017/004943 A1 which is being incorporated by reference in its entirety in the present invention. The processing of amniotic fluid occurs in a variety of ways, many of the process steps can damage the amniotic fluid and reduce its potential for maintaining its biological activity in particular its growth factors. The process of removing debris and unwanted particles from amniotic fluid as a result can also cause a loss of the biologic beneficial effects of the material. In some cases, the material is processed to a point that is simply represents virtually sterile water when completed and may have no medical value. The present invention, on the other hand, is relying on the use of amniotic fluid that has been processed in such a way that the material will maintain its biological growth factors that are commonly found in the native amniotic fluids. What is unique about the present invention is that this invention establishes that there are differences in amniotic fluids based on the fetal source. In particular, amniotic fluid is recovered from a mother planning to have a live birth pre-planned C-section. The amniotic fluid is recovered typically at 38 weeks from the pregnant mothers and provided in batches for sterilization. It is believed that this timing is somewhat arbitrary and could vary within a few weeks one side or the other of 38 weeks, for example 36 to 40 weeks could also provide amniotic fluid. In any event, the source of the amniotic fluid has always been simply the fluid surrounding the fetus that is withdrawn and typically used to be discarded and is now provided for use in soft tissue treatments and other treatments.

What was of interest to the present inventor was whether or not there was any significant difference between the amniotic fluids of a male fetus vs a female fetus. In other words, there was a speculation by the inventor that it may make a difference whether or not the fetal source of the amniotic fluid was a male or female. As a result of this, the inventor investigated sampling amniotic fluid that was selected based on the gender of the fetus. Although Amniotic Fluid has been around since the inception of humans, and Amniotic Fluid as a treatment has been around for close to 10 years, no one has ever looked at the fetal Gender as being a factor that differentiates the amniotic fluid. And its ability to treat diseases as a whole or certain diseases. This is not obvious and very unique. In doing so, it was discovered that recovered amniotic fluid analysed using mass spectrometry had about 1500 growth factors and cytokines discovered. To be exact 1451 were reported in this study. In this study, it was also reported that there were 49 growth factors that were statistically significantly more present in Female Amniotic Fluid and 45 growth factors statistically significantly more present in Male amniotic fluid. Accordingly, it was established that there is a difference in the amniotic fluid based on the gender source of the fetus. This is a significant finding in that the amniotic fluid from one gender source may achieve beneficial results in certain treatments superior to those of the opposite gender. This has never been conceived of or done before in the literature.

To test this theory, the inventor decided to treat patients' penises who exhibited either erectile dysfunction or Peyronie's disease. In doing so, the amniotic fluid was infected using a blind study wherein the urologist and the physician injecting had no idea which gender fetal source the amniotic fluid came from, but only provided direct injections into the penis. The penile peak systolic velocities of the patients' pre-injection and post-injection were tested. In the study it was determined that the amniotic fluid based on the gender of the fetal source of the amniotic fluid provided different growth factors that would have an effect on erectile dysfunction and Peyronie's disease. To the surprise of the inventor, the gender based amniotic fluid did have a very unexpected result in which the inventor found that female amniotic fluid was statistically significantly better than the male amniotic fluid in treating Erectile Dysfunction and improving Penile Peak Systolic Velocity (P<0.05), P=0.012. To the inventor, who is skilled in the art, this was incredible and unobvious and extremely novel.

Similarly, the inventor discovered that the female sourced amniotic fluid seemed to improve Peyronie' s disease better. However, enough patients have not been tested to date to establish a clear confirmation that this is true. However, it is believed to have a similar beneficial effect superior to the effect of the male sourced amniotic fluid. In Peyronie' s Disease, Matrix Metalloprotinease Inhibition is important but can be stopped by TGF Beta. Female Amniotic Fluid has more tissue inhibitors of matrix metalloproteinase (TIMP) expression than male and may play an important role in helping with Peyronie's Disease. Also Male Amniotic Fluid works on the TGF Beta receptor so may play equally as important a role.

The inventor believes that the use of amniotic fluid differentiated by the gender of the fetus has never been done before Amniotic fluid that was sourced from either a female or male fetus is believed to provide unique treatments for specific diseases such as the cases exhibited for erectile dysfunction and Peyronie's disease that would be benefited greatly by the use of female amniotic fluid based on the 49 growth factors occurring in higher concentrations in that fluid source. Interestingly, females have a lower rate of Sudden Infant Death Syndrome (SIDS), and it is unknown why this is. Females also have a significantly higher amount of NP_001142.2 in their amniotic fluid that can prevent Sudden Infant Death Syndrome. One possible treatment of infants at high risk for SIDS is female specific Amniotic Fluid Nebulizers and Inhalers. Alternatively, it is believed that male amniotic fluid would have better results treating or preventing other diseases, such as Pulmonary Chronic Obstructive Pulmonary Diseases, or Wound healing. This is based upon the gene charting we did by putting these genes in certain functional categories for our abstract that was accepted to the Society of Sexual Medicine Conference this year. In any event, it is clear that there are distinctions in patient treatments based on the gender source of the amniotic fluid. As a result, the present invention is directed to this ability to source amniotic fluid based on gender of the source. This invention can explain why sometimes physicians claim their amniotic fluid patient results are unreliable, when amniotic fluid is used as a treatment. It is likely dependent on the gender of the amniotic fluid fetus and the disease process being treated.

TABLE 1

Growth Factors, Proteins, Female Dominant

| Growth Factors and Proteins | Abundance Ratio P-Value: (male)/(female) | Abundance Ratio Adj. P-Value: (male)/(female) |
|---|---|---|
| NP_001306130.1 protein S100-A8 isoform d [Homo sapiens] S100A8 | 0.305 | 0.005510287 |
| NP_002956.1 protein S100-A9 [Homo sapiens] S100A9 | 0.278 | 0.002675392 |
| NP_065723.1 protein S100-A14 [Homo sapiens] S100A14 | 0.214 | 0.000273433 |
| NP_005611.1 protein S100-A11 [Homo sapiens] S100A11 | 0.258 | 0.001497062 |
| NP_005538.2 involucrin [Homo sapiens] IVL | 0.215 | 0.00029255 |
| XP_016870146.1 annexin A1 isoform X1 [Homo sapiens] ANXA1 | 0.208 | 0.000211106 |
| NP_001531.1 heat shock protein beta-1 [Homo sapiens] HSPB1 | 0.3 | 0.004865982 |
| NP_001303936.1 protein S100-A16 [Homo sapiens] S100A16 | 0.232 | 0.000582268 |
| NP_000415.2 keratin, type II cytoskeletal 5 [Homo sapiens] KRT5 | 0.249 | 0.001099551 |
| NP_775109.2 keratin, type II cytoskeletal 6C [Homo sapiens] KRT6C; KRT6A | 0.214 | 0.000295615 |
| NP_057274.1 cornulin [Homo sapiens] CRNN | 0.189 | 8.49595E−05 |
| NP_002263.3 keratin, type II cytoskeletal 4 [Homo sapiens] KRT4 | 0.079 | 1.32454E−09 |
| NP_705694.2 keratin, type I cytoskeletal 13 isoform a [Homo sapiens] KRT13 | 0.075 | 6.08683E−10 |
| NP_002267.2 keratin, type I cytoskeletal 19 [Homo sapiens] KRT19 | 0.16 | 1.40704E−05 |
| NP_005545.1 keratin, type II cytoskeletal 6C [Homo sapiens] KRT6A | 0.131 | 1.34666E−06 |
| NP_001435.1 fatty acid-binding protein, epidermal [Homo sapiens] FABP5 | 0.254 | 0.001280949 |

TABLE 1-continued

Growth Factors, Proteins, Female Dominant

| Growth Factors and Proteins | Abundance Ratio P-Value: (male)/(female) | Abundance Ratio Adj. P-Value: (male)/(female) |
|---|---|---|
| NP_000587.1 insulin-like growth factor-binding protein 1 precursor [Homo sapiens] IGFBP1 | 0.248 | 0.001059966 |
| NP_443112.2 phosphoinositide-3-kinase-interacting protein 1 isoform 1 precursor [Homo sapiens] PIK3IP1 | 1.285 | 0.472931274 |
| NP_001979.2 envoplakin isoform 2 [Homo sapiens] EVPL | 0.275 | 0.002473144 |
| NP_001116437.1 repetin [Homo sapiens] RPTN | 0.149 | 5.69435E−06 |
| NP_057215.3 ras-related protein Rab-10 [Homo sapiens] RAB10 | 0.299 | 0.004452985 |
| NP_001171712.1 voltage-dependent anion-selective channel protein 2 isoform 1 [Homo sapiens] VDAC2 | 0.225 | 0.000445982 |
| XP_005259194.1 40S ribosomal protein S16 isoform X1 [Homo sapiens] RPS16 | 0.294 | 0.003044342 |
| NP_001142.2 ADP/ATP translocase 1 [Homo sapiens] SLC25A4 | 0.254 | 0.001107207 |
| NP_009140.1 60S ribosomal protein L35 [Homo sapiens] RPL35 | 0.178 | 3.5374E−05 |
| NP_057671.2 chromobox protein homolog 3 [Homo sapiens] CBX3; C15orf57; CCDC32 | 0.229 | 0.00052652 |
| NP_071404.2 p53 apoptosis effector related to PMP-22 [Homo sapiens] PERP | 0.181 | 3.31804E−05 |
| NP_001001973.1 ATP synthase subunit gamma, mitochondrial isoform L (liver) precursor [Homo sapiens] ATP5C1 | 0.277 | 0.002331947 |
| NP_114409.2 plasma alpha-L-fucosidase precursor [Homo sapiens] FUCA2 | 0.15 | 9.52609E−06 |
| NP_001132929.1 B-cell receptor-associated protein 31 isoform a [Homo sapiens] BCAP31 | 0.272 | 0.001161581 |
| NP_001135757.1 40S ribosomal protein S24 isoform d [Homo sapiens] RPS24 | 0.256 | 0.000823958 |
| NP_002943.2 40S ribosomal protein S2 [Homo sapiens] RPS2 | 0.301 | 0.003440049 |
| NP_005637.3 probable methyltransferase TARBP1 [Homo sapiens] TARBP1 | 0.271 | 0.00199776 |
| NP_001276737.1 alpha-crystallin B chain isoform 1 [Homo sapiens] CRYAB | 0.196 | 0.000120054 |
| NP_001313.1 cystatin-SA precursor [Homo sapiens] CST2 | 0.206 | 0.000191209 |
| NP_444513.1 dermcidin isoform 1 preproprotein [Homo sapiens] DCD | 0.232 | 0.000583814 |
| NP_001186757.1 cornifin-A [Homo sapiens] SPRR1A | 0.212 | 0.000187342 |
| XP_016880078.1 junction plakoglobin isoform X1 [Homo sapiens] JUP | 0.208 | 0.000211514 |
| NP_002696.3 periplakin [Homo sapiens] PPL | 0.274 | 0.002423476 |
| NP_001186652.1 cellular retinoic acid-binding protein 2 [Homo sapiens] CRABP2 | 0.269 | 0.002099494 |
| NP_004406.2 desmoplakin isoform I [Homo sapiens] DSP | 0.212 | 0.000257882 |
| XP_016873759.1 neuroblast differentiation-associated protein AHNAK isoform X2 [Homo sapiens] AHNAK | 0.292 | 0.003976564 |
| NP_002266.2 keratin, type I cytoskeletal 15 [Homo sapiens] KRT15 | 0.215 | 0.000291601 |
| NP_001005337.1 plakophilin-1 isoform 1a [Homo sapiens] PKP1 | 0.193 | 0.000103096 |
| XP_016881722.1 choriogonadotropin subunit beta variant 1 isoform X1 [Homo sapiens] CGB1 | 0.248 | 0.001052441 |
| NP_056932.2 keratin, type II cytoskeletal 2 oral [Homo sapiens] KRT76 | 0.154 | 9.09917E−06 |
| NP_002855.2 pregnancy zone protein precursor [Homo sapiens] PZP | 0.269 | 0.002069415 |
| NP_005969.1 protein S100-A2 [Homo sapiens] S100A2 | 0.163 | 1.22605E−05 |

TABLE 1-continued

Growth Factors, Proteins, Female Dominant

| Growth Factors and Proteins | Abundance Ratio P-Value: (male)/(female) | Abundance Ratio Adj. P-Value: (male)/(female) |
|---|---|---|
| NP_000688.2 arachidonate 12-lipoxygenase, 12S-type [Homo sapiens] ALOX12 | 0.158 | 1.24344E−05 |

With reference to table 1, this table shows and identifies 49 attributes such as growth factors and proteins in a first column that are of a higher proportion when gender specific amniotic fluid is from a female fetal source. The adjacent column reflects a ratio of the male/female proportions each of the attributes. As shown, all are substantially below 1. These listed growth factors and proteins are in a higher concentration than from a male fetal source as shown in the chart. These are in the second column called: "Abundance Ratio P-Value:(male)/(female)" (AA). The third column called "Abundance Ratio Adj P-Value:(male)/(female)" (AB). In this column, each protein is measured and adjusted to all 1451 proteins measured versus one individual protein. It is compared to all other proteins such that there is no random chance a specific one is elevated.

The P value used to determine statistically significant differences was P<0.005. This is much more stringent than a usual P value of P<0.05. Some of these are over 10 times greater in female than male amniotic fluid.

TABLE 2

| Growth Factors and Proteins | Abundance Ratio P-Value: (male)/(female) | Abundance Ratio Adj. P-Value: (male)/(female) |
|---|---|---|
| NP_036246.1 caspase-14 precursor [Homo sapiens] CASP14 | 4.37 | 0.000224368 |
| NP_002007.1 filaggrin [Homo sapiens] FLG | 10.982 | 3.09098E−09 |
| NP_001153392.1 vascular endothelial growth factor receptor 1 isoform 2 precursor [Homo sapiens] FLT1 | 2.966 | 0.002397936 |
| NP_001159921.1 inter-alpha-trypsin inhibitor heavy chain H4 isoform 2 precursor [Homo sapiens] ITIH4 | 2.769 | 0.0035595 |
| NP_076956.1 gamma-glutamylcyclotransferase isoform 1 [Homo sapiens] GGCT | 2.979 | 0.005795033 |
| NP_000377.1 bleomycin hydrolase [Homo sapiens] BLMH | 4.012 | 0.000497011 |
| NP_001289194.1 neutrophil defensin 1 isoform 1 preproprotein [Homo sapiens] DEFA1B; DEFA1 | 3.124 | 0.002654632 |
| NP_005971.1 protein S100-P [Homo sapiens] S100P | 2.689 | 0.005140474 |
| NP_059118.2 calmodulin-like protein 5 [Homo sapiens] CALML5 | 5.621 | 1.70252E−05 |
| NP_001014364.1 filaggrin-2 [Homo sapiens] FLG2 | 6.251 | 5.14524E−06 |
| XP_005266835.2 serpin B12 isoform X1 [Homo sapiens] SERPINB12 | 3.945 | 0.000579305 |
| NP_001231367.1 arginase-1 isoform 1 [Homo sapiens] ARG1 | 3.528 | 0.001526005 |
| NP_009175.2 proline-rich protein 4 isoform 2 precursor [Homo sapiens] PRR4 | 2.936 | 0.006442024 |
| NP_778253.2 keratin, type II cytoskeletal 1b [Homo sapiens] KRT77 | 4.349 | 0.000235064 |
| NP_006323.2 gamma-interferon-inducible lysosomal thiol reductase preproprotein [Homo sapiens] IFI30 | 4.058 | 0.000140941 |
| NP_002621.1 gastricsin isoform 1 preproprotein [Homo sapiens] PGC | 3.343 | 0.002374363 |
| NP_001963.1 neutrophil elastase preproprotein [Homo sapiens] ELANE | 4.989 | 6.04516E−05 |
| XP_011534801.1 cathepsin G isoform X1 [Homo sapiens] CTSG | 2.909 | 0.00365075 |
| NP_001180262.1 coronin-1A [Homo sapiens] CORO1A | 3.38 | 0.001023141 |
| NP_005441.1 noggin precursor [Homo sapiens] NOG | 4.593 | 4.59596E−05 |
| NP_006240.4 basic salivary proline-rich protein 3 precursor [Homo sapiens] PRB3 | 2.809 | 0.003799462 |
| NP_001019850.1 skin-specific protein 32 [Homo sapiens] C1orf68 | 2.804 | 0.005355183 |
| NP_001691.1 azurocidin preproprotein [Homo sapiens] AZU1 | 4.412 | 7.21396E−05 |
| XP_011541136.1 neutrophil collagenase isoform X1 [Homo sapiens] MMP8 | 3.942 | 0.000115751 |
| XP_005247417.1 lysosome-associated membrane glycoprotein 3 isoform X1 [Homo sapiens] LAMP3 | 3.005 | 0.00207313 |
| NP_068741.1 Fanconi anemia group E protein [Homo sapiens] FANCE | 2.955 | 0.002748764 |
| NP_002143.1 sarcoplasmic reticulum histidine-rich calcium-binding protein precursor [Homo sapiens] HRC | 3.064 | 0.002018187 |
| NP_064581.2 pre-mRNA-splicing factor SYF1 [Homo sapiens] XAB2 | 3.954 | 0.000216534 |

TABLE 2-continued

| Growth Factors and Proteins | Abundance Ratio P-Value: (male)/(female) | Abundance Ratio Adj. P-Value: (male)/(female) |
|---|---|---|
| XP_011525801.1 dermokine isoform X4 [Homo sapiens] DMKN | 26.879 | 1E-17 |
| NP_002768.3 myeloblastin precursor [Homo sapiens] PRTN3 | 4.328 | 0.000312229 |
| XP_011525797.1 dermokine isoform X1 [Homo sapiens] DMKN | 14.715 | 2.03593E-12 |
| NP_775103.1 small proline-rich protein 4 [Homo sapiens] SPRR4 | 5.601 | 2.88672E-06 |
| NP_291031.2 guanylin precursor [Homo sapiens] GUCA2A | 3.142 | 0.001370691 |
| NP_991403.1 lipolysis-stimulated lipoprotein receptor isoform 2 [Homo sapiens] LSR | 3.435 | 0.001902331 |
| NP_001138479.1 mucin-7 precursor [Homo sapiens] MUC7 | 4.217 | 0.000314174 |
| NP_002414.1 matrilysin preproprotein [Homo sapiens] MMP7 | 3.949 | 0.000223214 |
| NP_002099.1 histidine ammonia-lyase isoform 1 [Homo sapiens] HAL | 3.374 | 0.002201512 |
| XP_016864371.1 chloride intracellular channel protein 6-like [Homo sapiens] LOC107986211 | 3.128 | 0.001518546 |
| NP_000418.2 loricrin [Homo sapiens] LOR | 3.776 | 0.000853704 |
| NP_543145.1 WAP four-disulfide core domain protein 12 precursor [Homo sapiens] WFDC12 | 13.268 | 2.77156E-12 |
| NP_001078851.1 proactivator polypeptide-like 1 preproprotein [Homo sapiens] PSAPL1 | 2.985 | 0.005700476 |
| XP_011546040.1 major histocompatibility complex, class II, DR beta 1 isoform X1 [Homo sapiens] HLA-DRB3; LOC100507709; LOC100507714; LOC105369230; HLA-DRB1 | 2.844 | 0.005070247 |

As shown in table 2, is a second table showing and identifying the 42 attributes such as growth factors and proteins that are in a higher proportion when gender specific amniotic fluid is from a male fetal source than a female fetal specific source. In this case, the male fetal source amniotic fluid has a higher percentage of these growth factors and proteins when compared to a female fetal source amniotic fluid. Some of these are over 10 times greater in male than female amniotic fluid. As shown in table 2, the abundance ratio of male/female is substantially greater than 1.0.

Figure 1:
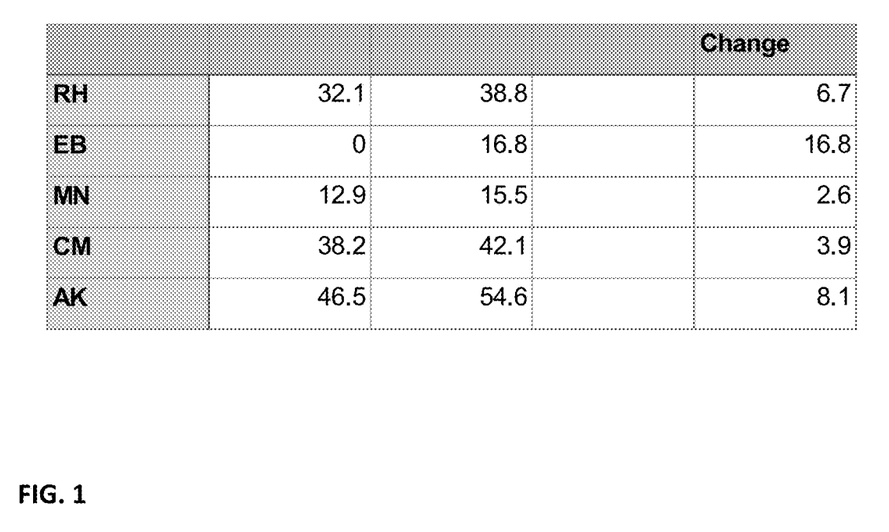
FIG. 1 is a table showing the PSV wherein Female amniotic fluid was statistically significantly better than the male in treating Erectile Dysfunction and improving Penile Peak Systolic Velocity (P<0.05), P=0.012.

With reference to FIG. 1, a table is shown for the PSV, wherein the female fetal source amniotic fluid was statistically significantly better than the male fetal source amniotic fluid when treating erectile dysfunction and improving Penile Peak Systolic Velocity as discussed above.

It is believed that this discovery and resultant amniotic fluid product based on gender can provide unique treatments. Such treatments can be provided as ointment based for treating wounds and other soft tissue. Alternatively, treatments can be provided as a fluid for direct injection as was the case in the study on erectile dysfunction and Peyronie's' disease. The fluid can also be supplied as a nebulized or aerosolized treatment or suppository.

Figure 2:
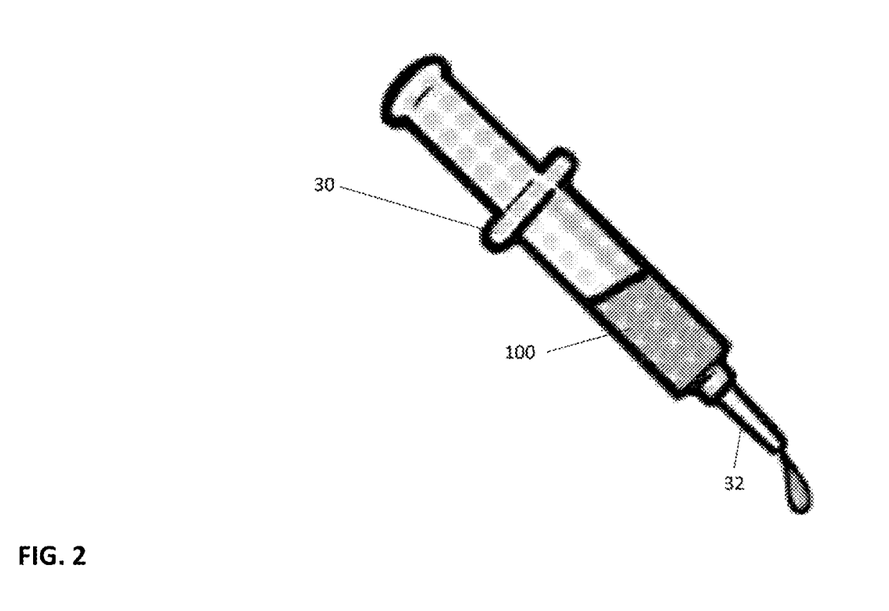
FIG. 2 is a perspective view of a syringe with the amniotic fluid suitable for direct injection.
Figure 3:
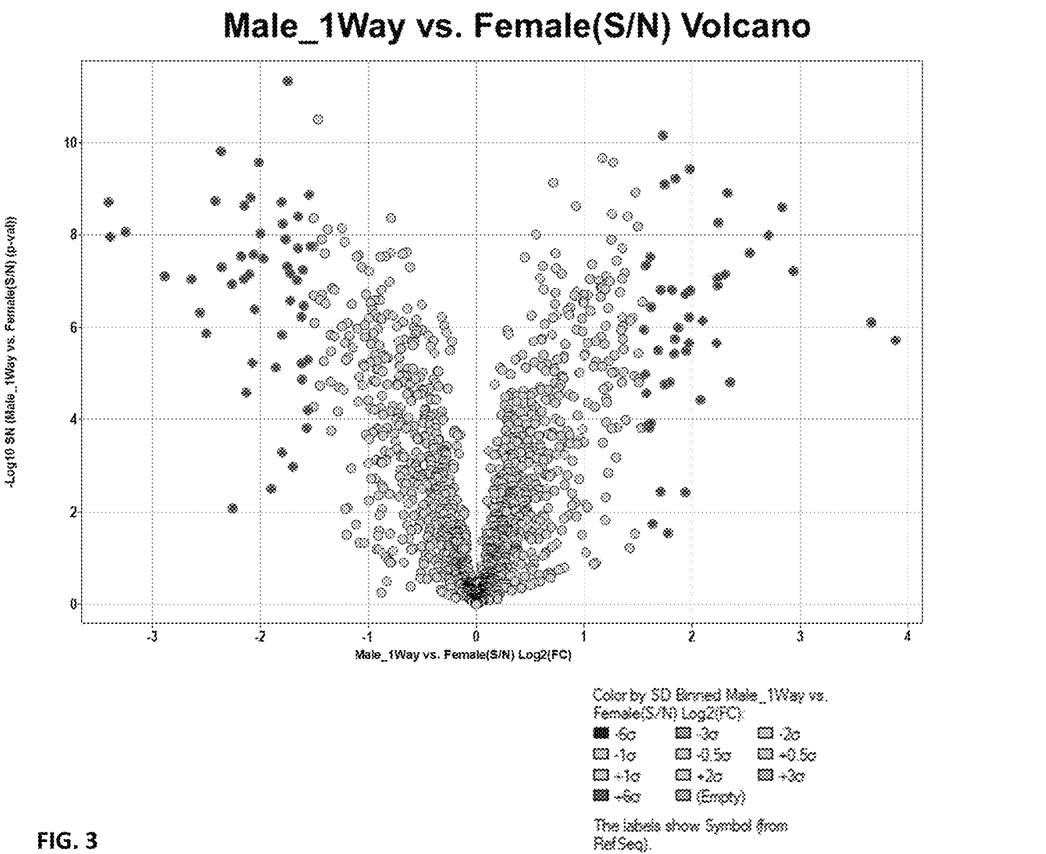
FIG. 3 is a volcano plot graph showing male_1 way versus female (s/n) Volcano.
Figure 4:
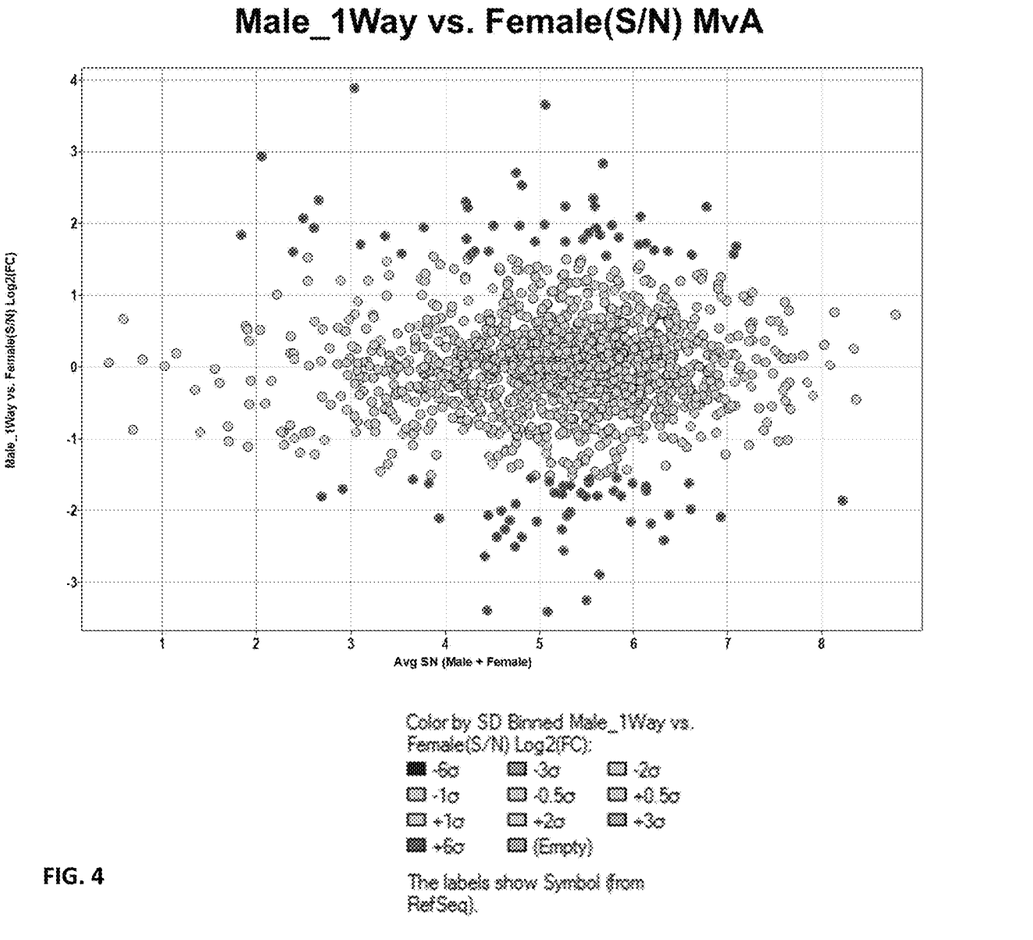
FIG. 4 is a volcano plot graph showing male_1 way versus female (s/n) MvA.
Figure 5:
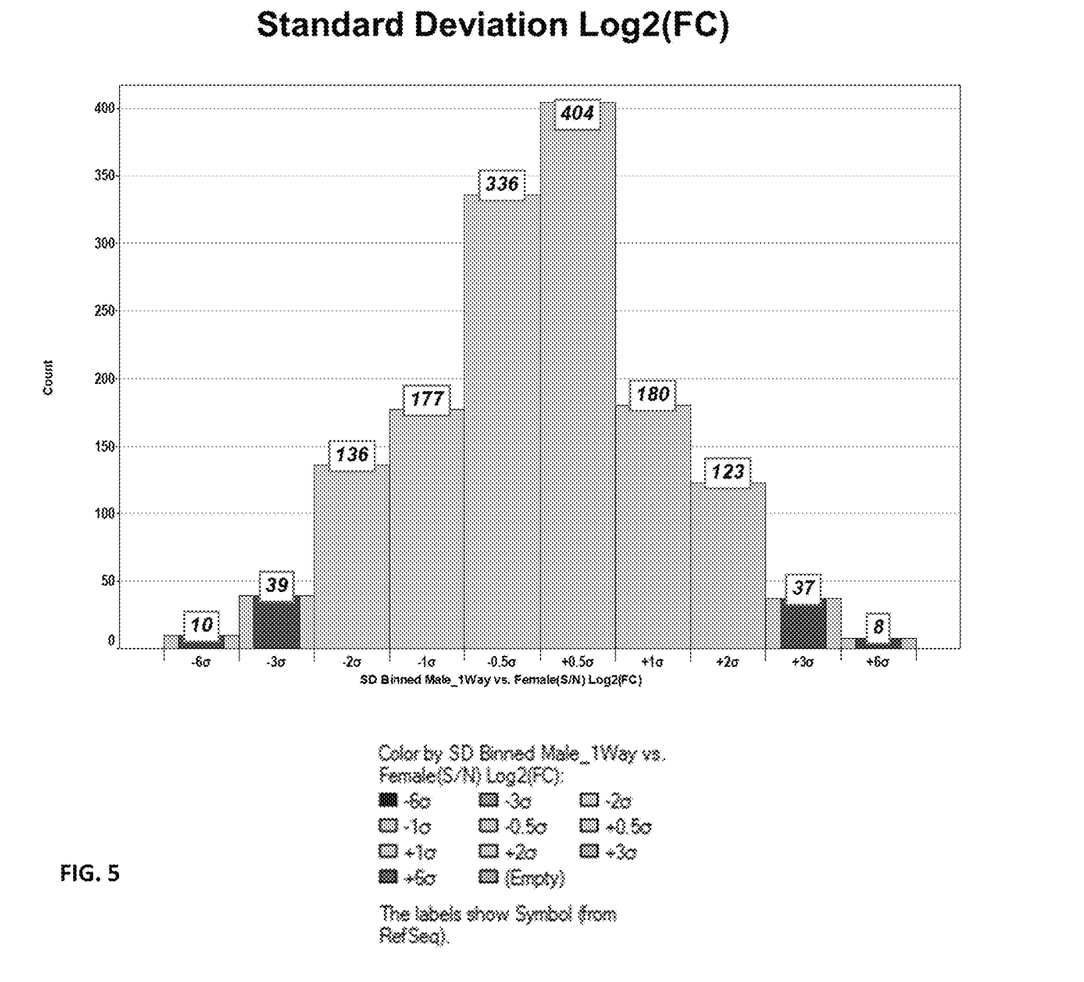
FIG. 5 is a graph showing standard deviation log 2 (FC).
Figure 6:
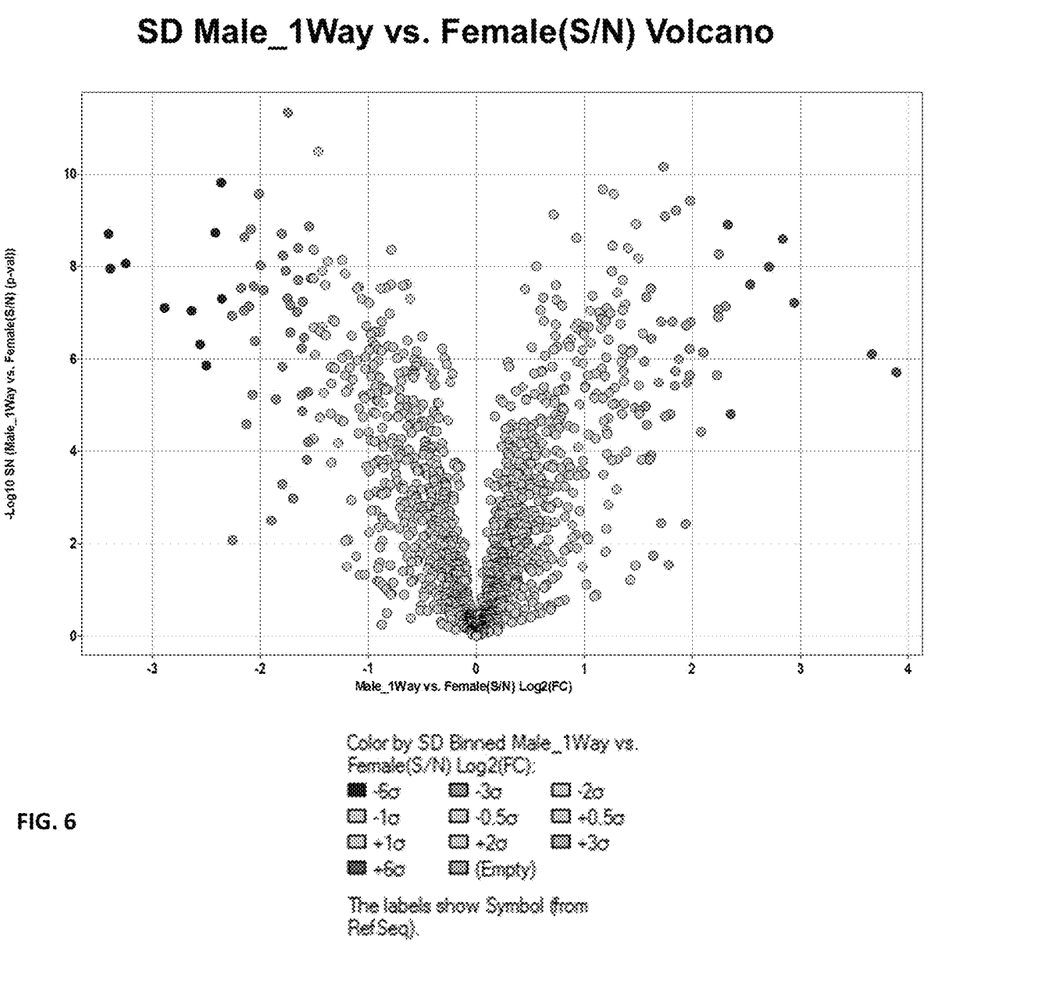
FIG. 6 SD male_1 way versus female (s/n) Volcano.
Figure 7:
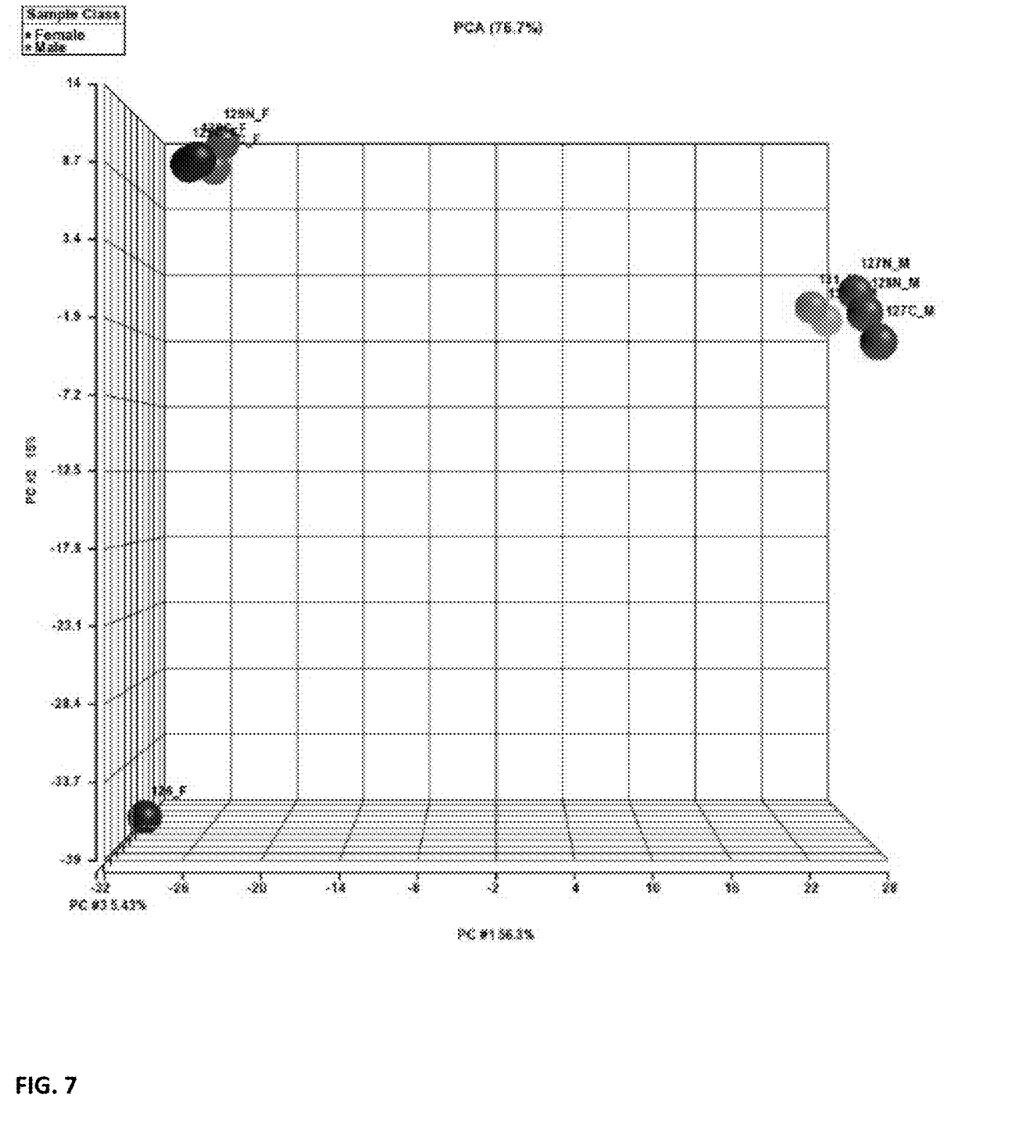
FIG. 7 is a PCA graph.
Figure 8:
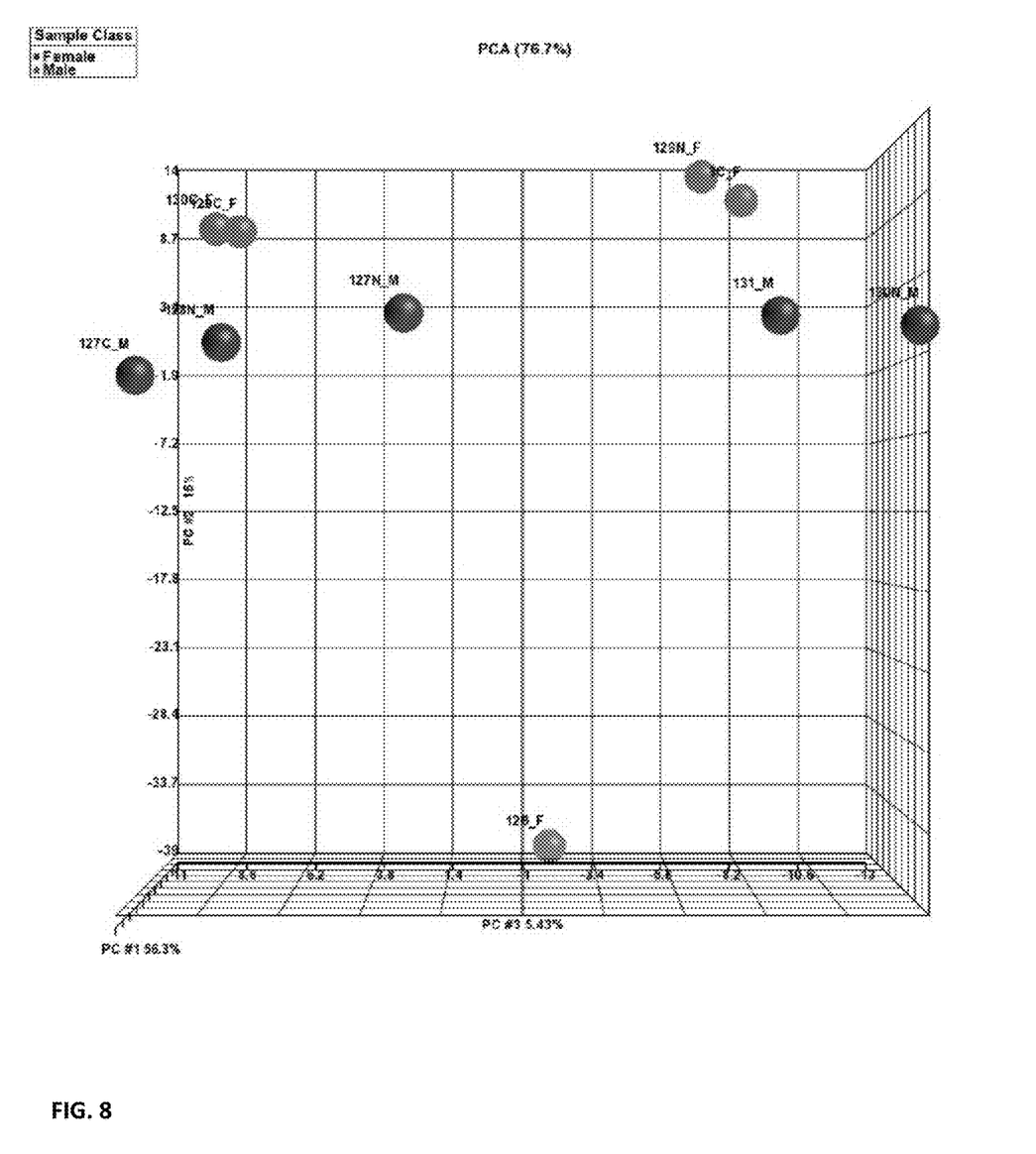
FIG. 8 is a PCA graph.
Figure 9:
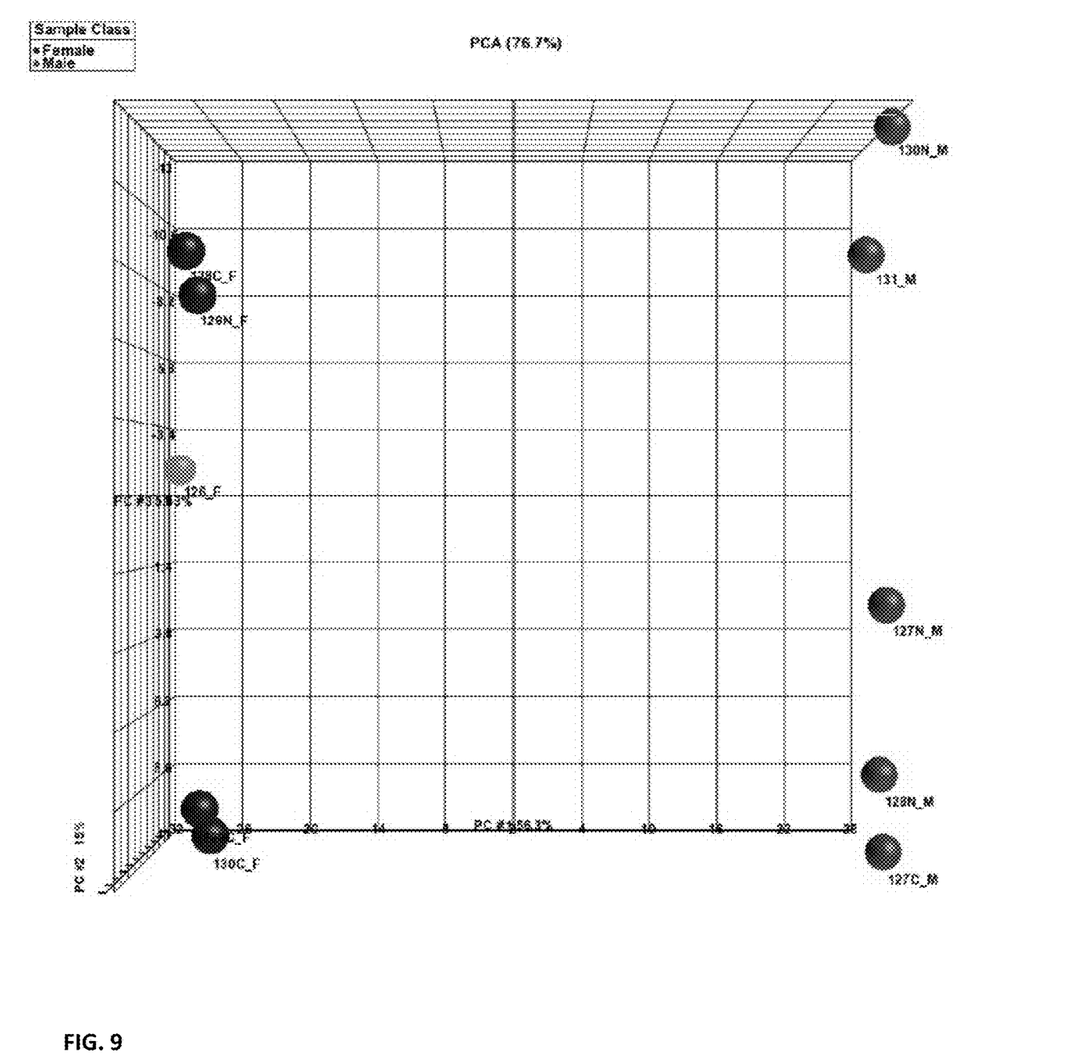
FIG. 9 is a PCA graph.

With reference to FIG. 2, an exemplary syringe 30 with needle 32 is shown with an amount of amniotic fluid 100 suitable injection based on the gender of fetal source.

It is important to note that during the analysis of amniotic fluid that the growth factors exhibited are interesting, some dealing with sudden infant death syndrome and may be useful in identifying precursors to such an event. Importantly, it is believed the ability to differentiate growth factors of amniotic fluid based on gender of the fetal source will be of value as it is applied to treating specific disease. Of note, most of the growth factors and cytokines deal with metabolic pathways and cell proliferation, cell differentiation, and cell death. As a result, it is believed that a sterile supply of amniotic fluid based on gender may result in unique treatment protocols heretofore not attempted. The results revealed one growth factor predominantly more in FEMALES, XP_016881722.1, that is a Choriogonadotropin, which is believed to be important.

It is believed that a physician, knowing the differences in specific growth factors, can select from one or more of the gender differentiated amniotic fluids to select the one with the highest concentrations of these more prevalent growth factors and proteins to achieve the desired treatment results. Heretofore this has not been done. This is similar to stem cell research where individual cells are noted by their expressed marker. In this case the amniotic fluid is being distinguished based on its increased percentages of specific growth factors which would then be used to determine which gender based amniotic fluid can be used in particular treatments. In other words, this unique discovery is the first step in determining targeted biological exosome and growth factor therapy for diseases. Since we are able to isolate in higher concentrations specific growth factors and exosomes and cytokines with minimal manipulation of the Amniotic Fluid.

The composition and method of the present invention can be used in combination with compositions and methods in U.S. Ser. Nos. 15/158,101; 14/363,142; and 15/541,988 all of which are being incorporated herein by reference in their entirety in the present invention.

With reference to FIGS. 3-9, graphs and volcano plots are shown that illustrate differences between male and female samples of the gender specific amniotic fluid, female is indicated by blue or F and male is indicated in red or M.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of treating a patient with a tissue disease or malformity comprises the steps of:
   identifying a tissue region to be treated and selecting a location to apply either topically or by injection a composition containing amniotic fluid, wherein the tissue disease or malformity is in a penis;
   selecting the composition containing amniotic fluid wherein the amniotic fluid comprising a quantity of gender specific amniotic fluid based on a gender of a fetal source, wherein the gender specific amniotic fluid of a female fetal source or a male fetal source exhibits a total of about 1500 growth factors and cytokines when tested under mass spectrometry; each gender specific amniotic fluid of a female fetal source exhibiting a number of growth factors differing in concentration from a male fetal source wherein the female fetal source amniotic fluid exhibits a number of growth factors in a higher concentration than the male fetal source amniotic fluid and wherein each of the number of growth factors concentration higher in each gender specific amniotic fluid is greater than 25 and less than 50 of the total of about 1500 and the selected composition with amniotic fluid for the penis is the female fetal source amniotic fluid and 5 or more of the following growth factors or proteins are present in the female fetal source amniotic fluid: NP_001306130.1 protein S100-A8 isoform d, NP_002956.1 protein S100-A9, NP_065723.1 protein S100-A14, NP_005611.1 protein S100-A11, NP_005538.2 involucrin, XP 016870146.1 annexin Al isoform Xl, NP_001531.1 heat shock protein beta-1, NP_001303936.1 protein S100-A16, NP_000415.2 keratin, type II cytoskeletal 5, NP_775109.2 keratin, type II cytoskeletal 6C, NP_057274.1cornulin, NP_002263.3 keratin, type II cytoskeletal 4, NP_705694.2 keratin, type I cytoskeletal 13 isoform a, NP_002267.2 keratin, type I cytoskeletal 19, NP_005545.1 keratin, type II cytoskeletal 6C, NP_001435.1 fatty acid-binding protein, epidermal, NP_000587.1 insulin-like growth factor-binding protein 1 precursor, NP_001276737.1 alpha-crystallin B chain isoform 1, NP_001313.1 cystatin-SA precursor, NP_444513.1 dermcidin isoform 1 preproprotein, NP_001186757.1 cornifin-A, XP_016880078.1 junction plakoglobin isoform Xl, NP_002696.3 periplakin, NP_001186652.1 cellular retinoic acid-binding protein 2, NP_004406.2 desmoplakin isoform I, XP 016873759.1 neuroblast differentiation-associated protein AHNAK isoform X2, NP_002266.2 keratin, type I cytoskeletal 15, NP_001005337.1 plakophilin-1 isoform 1a, XP_016881722.1 choriogonadotropin subunit beta variant 1 isoform Xl, NP_056932.2 keratin, type II cytoskeletal 2 oral, NP_002855.2 pregnancy zone protein precursor, NP_005969.1 protein S100-A2, NP_000688.2 arachidonate 12-lipoxygenase, 12S-type, NP_443112.2 phosphoinositide-3-kinase-interacting protein 1 isoform 1 precursor, NP_001979.2 envoplakin isoform 2, NP_001116437.1 repetin, NP_057215.3 ras-related protein Rab-10, NP_001171712.1 voltage-dependent anion-selective channel protein 2 isoform 1, XP_005259194.1 40S ribosomal protein S16 isoform Xl, NP_001142.2 ADP/ATP translocase 1, NP_009140.1 60S ribosomal protein L35, NP_057671.2 chromobox protein homolog 3, NP_071404.2 p53 apoptosis effector related to PMP-22, NP_001001973.1 ATP synthase subunit gamma, mitochondrial isoform L (liver) precursor, NP_114409.2plasma alpha-L-fucosidase precursor, NP_001132929.1 B-cell receptor-associated protein 31 isoform a, NP_001135757.1 40S ribosomal protein S24 isoform d, NP_002943.2 40S ribosomal protein S2, NP_005637.3 probable methyltransferase TARBP1; those five or more growth factors in the female source exhibiting a higher ratio than those of a male source and wherein said five or more growth factors including XP_016881722.1 choriogonadotropin subunit beta variant 1 isoform Xl, NP_000587.1 Insulin-like growth factor-binding protein 1; prolongs the half-life of the IGFs and alters their interaction with cell surface receptors, NP_001531.1 Heat shock protein 27; provide thermotolerance in vivo, cyto-protection, and support of cell survival under stress conditions, stabilizing partially denatured proteins, protects actin filaments from fragmentation, XP_016870146.1 Annexin Al; inhibits various leukocyte inflammatory events, inhibit the two main products of inflammation, effect being much like that of NSAIDs, potentiating the anti-inflammatory effect, NP_000415.2 Keratin 5; in the stratified epithelium lining the skin and digestive tract forms the intermediate filaments (IF) that make up the cytoskeleton of basal epithelial cells, increases the elasticity; and applying or injecting the composition at or into the selected location.

2. The method of claim 1 wherein the female fetal source amniotic fluid has 49 growth factors statistically significantly greater than the male fetal source amniotic fluid.

3. The method of claim 1 wherein the selection of the composition with amniotic fluid is guided by differences in growth factors and cytokines between the female fetal source amniotic fluid and the male fetal source amniotic fluid.

4. The method of claim 1 wherein the tissue disease or malformity is Peyronie's disease.

5. The method of claim 1 wherein the tissue disease is erectile dysfunction.

6. The method of claim 1 further comprising NP_005545.1 Keratin 6A; shown to have antimicrobial properties, and is the main antimicrobial factor in the eye, NP_001276737 Alpha-crystallin B chain; bind improperly folded proteins to prevent protein aggregation, confer stress resistance to cells by inhibiting the processing of the pro-apoptotic protein caspase-3, increased during various stresses, which then may lead to prolonged survival of cells under these conditions, NP_001313.1 Cystatin-SA; found in a variety of human fluids and secretions, where they appear to provide protective functions, NP_444513.1 Dermcidin, anti-microbial peptides, secreted by human eccrine sweat glands onto the skin as a part of the innate host defense of the immune system, XP_016873759.1 Neuroblast differentiation-associated protein, neuronal differentiation, elasticity, structural scaffolding, and NP_002855.2 Pregnancy zone protein; role in immune-regulation during pregnancy.

* * * * *